United States Patent [19]

Seki et al.

[11] Patent Number: 4,968,708
[45] Date of Patent: Nov. 6, 1990

[54] IMIDAZO[2,1-B]BENZOTHIAZOLE COMPOUNDS AND ANTIULCER COMPOSITIONS CONTAINING THE SAME

[75] Inventors: Taketsugu Seki; Shigeyuki Tasaka; Ryuichi Hoshino, all of Saitama, Japan

[73] Assignee: Nikken Chemicals Co., Ltd., Tokyo, Japan

[21] Appl. No.: 369,392

[22] Filed: Jun. 21, 1989

[30] Foreign Application Priority Data

Jun. 22, 1988 [JP] Japan ............................. 63-152116

[51] Int. Cl.$^5$ .................. C07D 513/04; H61K 31/425
[52] U.S. Cl. ..................................... 511/366; 548/151
[58] Field of Search ......................... 548/151; 514/366

[56] References Cited

U.S. PATENT DOCUMENTS 4,497,817  2/1985  Murase ................. 548/151

FOREIGN PATENT DOCUMENTS 52-83586   7/1977   Japan ................. 548/151
56-68685   6/1981   Japan .
56-71096   6/1981   Japan .
56-138196  10/1981  Japan .
57-40492   3/1982   Japan ................. 548/151
57-149288  9/1982   Japan .
58-109491  6/1983   Japan .
59-78194   5/1984   Japan .
60-258184  12/1985  Japan .
62-48672   10/1987  Japan .

OTHER PUBLICATIONS

Il Farmaco-Ed.Sc.-vol. 36-fasc.10, pp. 893-904.

*Primary Examiner*—Robert Gerstl
*Attorney, Agent, or Firm*—Sughrue, Mion, Zinn, Macpeak & Seas

[57] ABSTRACT

The present invention relates to novel imidazo-[2,1-b]benzothiazole compounds represented by formula (I) and pharmacological acceptable salts thereof:

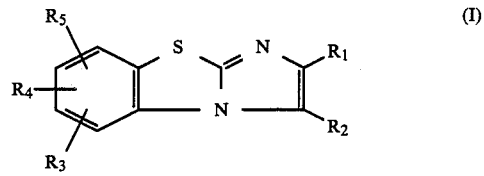

wherein $R_1$ represents a hydrogen atom or a lower alkyl group having 1 to 4 carbon atoms; $R_2$ represents a

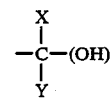

group (wherein X and Y, which may be the same or different, each represents a hydrogen atom, a lower alkyl group having 1 to 4 carbon atoms or a substituted or unsubstituted phenyl group), a —$CH_2$—O—Z group (wherein Z represents a lower alkyl group having 1 to 4 carbon atoms or a substituted or unsubstituted benzyl group) or a —$CH_2$—O—CO—W group (wherein W represents an alkyl group having 1 to 8 carbon atoms, an alkylamino group having 1 to 8 carbon atoms, a substituted or unsubstituted phenyl group or a thienyl group); and $R_3$; $R_4$ and $R_5$, which may be the same or different, each represents a hydrogen atom, a halogen atom or a lower alkoxy group having 1 to 4 carbon atoms, and antiulcer compositions comprising as the efective ingredient the compounds.

13 Claims, No Drawings

IMIDAZO[2,1-B]BENZOTHIAZOLE COMPOUNDS AND ANTIULCER COMPOSITIONS CONTAINING THE SAME

FIELD OF THE INVENTION

The present invention relates to novel imidazo[2,1-b]benzothiazole compounds and an antiulcer agent containing as the active ingredient the imidazo[2,1-b]benzothiazole compounds.

BACKGROUND OF THE INVENTION

In general, it is considered that peptic ulcers would be caused when an imbalance occurred between attack factors such as gastric juice, pepsin, etc., and mucus, bicarbonate ion secretion phase, blood flow or the like. Their development is specific to stomach and duodenum. Medical drug therapy for these peptic ulcers has been shifted from therapy laying stress on antiacidic agents or anticholinergic agents to therapy attaching importance to histamine $H_2$ receptor antagonists showing a strong acid secretion inhibitory activity by blocking wall cell receptors. However, it is reported in Marks, I. N. et al., "Ulcer healing and relapse rate after initial treatment with cimetidine or sucralfate", J. Clin. Gastroent., 3 (Suppl. 2), 163–165 (1981) and Martin, D. F. et al., "Difference in relapse rates of duodenal ulcer after healing with cimetidine or tripotassium dicitrato bismuthate", Lancet, I, 7–10 (1981) that when administration of the histamine $H_2$ receptor or antagonists was discontinued, relapse of ulcer was noted with high frequency.

In recent years, based on a new finding in the acid secrection mechanism in gastric wall cells and mucus protecting mechanism, antiulcer agents which inhibit $[H^+ - K^+]$ adenosine triphosphatase (ATPase) participating in the final stage during the course of acid secretion in wall cells and which prevent secretion of gastic juice have been proposed, for example, in JP-B-60-34956 (The term "JP-B" as used herein means an "examined Japanese patent publication").

On the other hand, turning to imidazo[2,1-b]benzothiazole derivatives, they are already known and recited in publications, for example, as drugs for treatment of diabetes (JP-A-52-83586 (The term "JP-A" as used herein means an "unexamined published Japanese patent application")), as immune function regulators (JP-B-62-48672, JP-A-56-68685, JP-A-56-71096, JP-A-56-138196, JP-A-57-40492, JP-A-57-149288, JP-A-58-109491, JP-A-59-78194, etc.), as 8-receptor blockers (JP-A-60-258184) and the like. However, no specific disclosure or even suggestion has been found on medical application as antiulcer compositions.

The present inventors have synthesized many analogous compounds using known benzothiazole compounds as starting materials and made extensive investigations on these compounds. As a result, it has been found that while imidazo[2,1-b]benzothiazole compounds according to the present invention have a chemical structure different from known drugs showing an antiulcer activity, the compounds exhibit an excellent antiulcer activity. The present invention has been achieved based on such findings.

SUMMARY OF THE INVENTION

An object of the present invention is to provide novel imidazo[2,1-b]benzothiazole compounds represented by the following formula (I) and pharmacologically acceptable salts thereof.

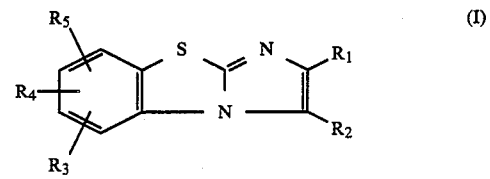

In the above formula (I), $R_1$ represents a hydrogen atom or a lower alkyl group having 1 to 4 carbon atoms; $R_2$ represents a

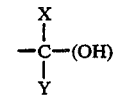

group (wherein X and Y, which may be the same or different, each represents a hydrogen atom, a lower alkyl group having 1 to 4 carbon atoms or a substituted or unsubstituted phenyl group), a —$CH_2$—O—Z group (wherein Z represents a lower alkyl group having 1 to 4 carbon atoms or a substituted or unsubstituted benzyl group) or a —$CH_2$—O—CO—W group (wherein W represents an alkyl group having 1 to 8 carbon atoms, an alkylamino group having 1 to 8 carbon atoms, a substituted or unsubstituted phenyl group or a thienyl group); and $R_3$, $R_4$ and $R_5$, which may be the same or different, each represents a hydrogen atom, a halogen atom or a lower alkoxy group having 1 to 4 carbon atoms.

Another object of the present invention is to provide antiulcer compositions comprising as the effective ingredient novel imidazo[2,1-b]benzothiazole compounds or pharmacologically acceptable salts thereof.

DETAILED DESCRIPTION OF THE INVENTION

The imidazo[2,1-b]benzothiazole compounds in accordance with the present invention are all novel compounds. The compounds and pharmacologically acceptable salts thereof are useful as antiulcer drugs in the medical field.

A first group of the compounds in accordance with the present invention which are represented by formula (I) are those wherein $R_1$ represents a hydrogen atom or a lower alkyl group having 1 to 4 carbon atoms; $R_2$ represents a

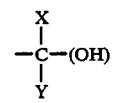

group (wherein X and Y, which may be the same or different, each represents a hydrogen atom, a lower alkyl group having 1 to 4 carbon atoms or a substituted or unsubstituted phenyl group, preferably a hydrogen atom; and $R_3$, $R_4$ and $R_5$, which may be the same or different, each represents a hydrogen atom, a halogen atom or a lower alkoxy group having 1 to 4 carbon atoms. Among the compounds of the above first group, compounds wherein $R_1$ represents a hydrogen atom or a lower alkyl group having 1 to 4 carbon atoms, preferably a methyl group, and $R_3$, $R_4$ and $R_5$ each represents a hydrogen atom are preferred.

A second group of the compounds in accordance with the present invention are those wherein $R_1$ represents a hydrogen atom or a lower alkyl group having 1 to 4 carbon atoms; $R_2$ represents a —$CH_2$—O—Z group (wherein Z represents a lower alkyl group having 1 to 4 carbon atoms or a substituted or unsubstituted benzyl group); and $R_3$, $R_4$ and $R_5$, which may be the same or different each represents a hydrogen atom, a halogen atom or a lower alkoxy group having 1 to 4 carbon atoms. Among the compounds of the above second group, compounds wherein $R_1$ represents a hydrogen atom or a lower alkyl group having 1 to 4 carbon atoms, preferably a methyl group, and $R_3$, $R_4$ and $R_5$ each represents a hydrogen atom are preferred.

A third group of the compounds in accordance with the present invention are those wherein $R_1$ represents a hydrogen atom or a lower alkyl group having 1 to 4 carbon atoms; $R_2$ represents a —$CH_2$—O—CO—W group (wherein W represents an alkyl group, an alkylamino group having 1 to 8 carbon atoms, a substituted or unsubstituted phenyl group or a thienyl group); and $R_3$, $R_4$ and $R_5$, which may be the same or different, each represents a hydrogen atom, a halogen atom or a lower alkoxy group having 1 to 4 carbon atoms. Among the compounds of the above third group, compounds wherein $R_1$ represents a hydrogen atom or a lower alkyl group having 1 to 4 carbon atoms, preferably a methyl group, and $R_3$, $R_4$ and $R_5$ each represents a hydrogen atom are preferred.

In the respective substituents defined by $R_1$ and $R_2$ in formula (I) described above, the term "lower alkyl group having 1 to 4 carbon atoms" refers to a straight or branched carbon chain having 1 to 4 carbon atoms. Specific examples thereof include a methyl group, an ethyl group, a n-propyl group, an isopropyl group, a n-butyl group, a sec-butyl group, a tert-butyl group, etc. The term "alkyl" used in "alkyl group having 1 to 8 carbon atoms" and "alkylamino group having 1 to 8 carbon atoms" refers to a straight or branched carbon chain having 1 to 8 carbon atoms. Specific examples thereof include, in addition to the lower alkyl groups described above, a pentyl group, a hexyl group, a heptyl group, an octyl group, etc. The terms "phenyl group" and "benzyl group" may be substituted with a lower alkyl group having 1 to 4 carbon atoms (e.g., the groups as described above), a lower alkoxy group having 1 to 4 carbon atoms (e.g., a methoxy group, an ethoxy group, a propoxy group or a butoxy group) or a halogen atom (e.g., a fluorine atom, a chlorine atom, a bromine atom or an iodine atom).

In the respective substituents defined by $R_3$, $R_4$ and $R_5$, examples of the halogen atom include a fluorine atom, a bromine atom, a chlorine atom or an iodine atom and examples of the lower alkoxy group include a methoxy group, an ethoxy group, a propoxy group, a butoxy group, etc.

The imidazo[2,1-b]benzothiazole derivatives represented by formula (I) which are provided by the present invention can be produced by the following processes.

Process I:

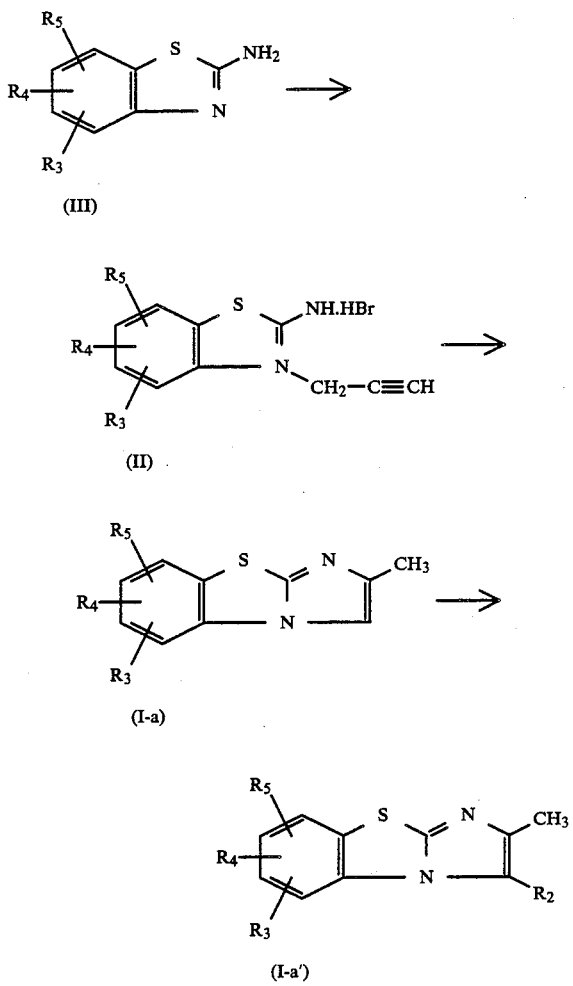

wherein $R_2$, $R_3$, $R_4$ and $R_5$ are as defined in formula (I).

Process II:

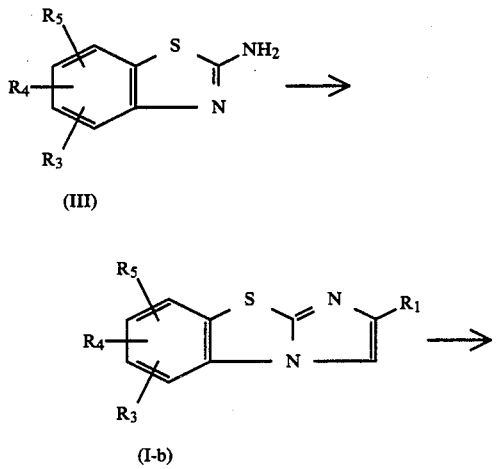

-continued
Process II:

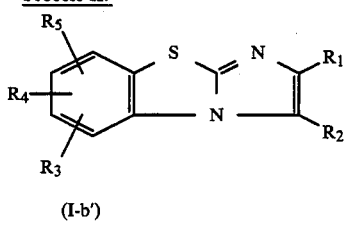

(I-b')

wherein $R_1$, $R_2$, $R_3$, $R_4$ and $R_5$ are as defined in formula (I).

That is, according to both Processes I and II, a 2-aminobenzothiazole derivative represented by formula (III) is used as the starting material and subjected to cyclization to produce the imidazo[2,1-b]benzothiazole derivative represented by formulae (I-a) or (I-a') or formulae (I-b) or (I-b').

These processes are described below in more detail. Either (1) a process which comprises reacting the 2-aminobenzothiazole derivative (III) with a propargyl halide in a solvent such as ethanol, n-butanol, ethylene glycol, etc., at a room temperature to 120° C., preferably 90° to 120° C., for 1 to 16 hours to convert the same into a 2-imino-3-propargylbenzothiazole derivative (II) and cyclyzing the derivative (II) in the alcohol in the presence of a condensing agent such as sodium hydroxide, a sodium alkoxide (Process I); or (2) a process which comprises reacting the 2-aminobenzothiazole derivative (III) with a halogenated ketone or a halogenated acetaldehyde in a solvent such as ethanol, n-butanol, methyl ethyl ketone, etc., at room temperature to 120° C., preferably 90° to 120° C., for 1 to 16 hours followed by cyclization (process II) can be appropriately chosen and applied. In these processes, the cyclized products may be subjected to the formylation and reduction processings or the reaction with amines in a formaldehyde solution.

The starting materials represented by formula (III) which is used in these processes are readily available to or can be readily synthesized by one skilled in the art, if necessary and desired. For example, they can be synthesized by methods as described, for example, in publications such as Journal of The Chemical Society, 127, 2023 (1925), Journal of The American Chemical Society, 58, 1364 (1936), Organic Syntheses, 22, 16 (1942), etc. For example, the compound represented by formula (III) can be produced by reacting the substituted aniline compound represented by formula (IV) with bromine in the presence of ammonium thiocyanate, potassium thiocyanate or sodium thiocyanate as described in *Journal of the Chemical Society*, page 268 (1989), Yakugaku Zasshi (Journal of Pharmacology), vol. 71, page 898 (1951), and *Yakuqaku Zasshi* (Journal of Pharmacology), vol. 77, page 645 (1957).

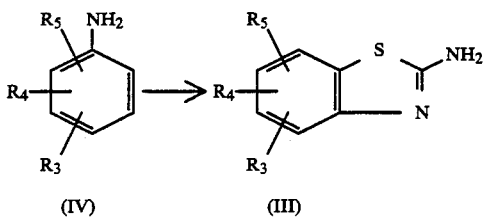

(IV)  (III)

($R_3$, $R_4$ and $R_5$ are as defined in formula (I)

Further, in the case of introducing a substituent, for example, at the 3-position of the compound represented by formula (I-a) or formula (I-b), a desired substituent can be introduced according to known reactions such as a Vilsmeier reaction or Mannich reaction, etc., to prepare the desired compound.

The imidazo[2,1-b]benzothiazole derivatives represented by formulae (I-a) and (I-a') or formulae (I-b) and (I-b') which are synthesized by the processes described above can be separated and purified from the reaction mixture in a conventional manner, for example, extraction with a solvent, chromatography, crystallization, etc.

Furthermore, the imidazo[2,1-b]benzothiazole derivative represented by formula (I) which can be produced by the processes described above can be converted into pharmacologically acceptable salts thereof, if necessary and desired. Examples of acid addition salts of these compounds are addition salts to inorganic acids such as hydrochloric acid, sulfuric acid, hydrobromic acid, etc.; addition salts to organic acids such as oxalic acid, citric acid, methanesulfonic acid, p-toluenesulfonic acid, etc. Examples of salts of these compounds with bases include salts with inorganic bases such as alkali metals (sodium, potassium, etc.); ammonium salts; salts with organic bases such as alkylamines, pyridine, etc. Accordingly, in the case of converting the imidazo[2,1-b]benzothiazole derivative represented by formula (I) into various pharmacologically acceptable salts thereof, for example, in the case of forming its acid addition salts, the compounds of the present invention are reacted with acids corresponding to the stoichiometrical amount in a suitable solvent to produce the salts.

The compounds produced in the present invention may involve optically active isomers such as dextrorotary and levorotary isomers and a mixture thereof, etc., and stereoisomers of cis and trans. All of these compounds are included within the scope of the present invention.

The compounds in accordance with the present invention posseses interesting pharmacological properties. Namely, the compounds of the present invention show a strong antiulcer activity against aspirin ulcer, water-immersion stress ulcer and ethanol ulcer in spite of the presence of aggressive factor inhibiting effect and/or mucosal defensive factor inhibiting effect. The compounds of the present invention have a low toxicity and are thus useful as therapeutic drugs such as an aggressive factor inhibiting agent or mucosal defensive factor inhibiting agent.

In the case of using the compounds in accordance with the present invention as antiulcer agents, the agents can be administered by an appropriate mode such as oral or parenteral route. Examples of oral administration include tablets, granules capsules, pills, powders, liquids, etc. For parenteral route, mention may be made of an injection, etc. In making these compositions for medical administration, the compound (and its salts) of the present invention can be formed into medical preparations in a conventional manner. For example, in the case of oral compositions, the compound may be formed into desired administration forms, using excipients such as lactose, glucose, corn starch, sucrose, etc.; disintegrators such as carboxymethyl cellulose calcium, hydroxypropyl cellulose, etc.; lubricants such as calcium stearate, magnesium stearate, talc, polyethylene glycol, hardened oil, etc.; binders such as hydroxypropylcellulose, hydroxypropylmethylcellulose, carboxymethylcellulose, polyvinyl alcohol, gelatin, gum arabic, etc.; wetting agents such as glycerine, ethylene glycol, etc.; and, if desired, surface active agents, corrigents, etc.

Further, in the case of parenteral compositions, the compound may be formed into parenteral preparations using diluents such as water, ethanol, glycerine, propylene glycol, polyethylene glycol, agar, tragacanth gum, etc., if desired, further using dissolution aids, buffers, preservatives, fragrances, coloring matters, etc.

In the case that the compound of the present invention is formulated as an antiulcer agent, the compound may be administered as a unit dose in a range of 50 to 800 mg, per day adult per preferably 100 to 400 mg, per adult per day in the case of oral administration and in the case of parenteral administration, in a range of 10 to 300 mg, preferably 30 to 200 mg, per adult per a day. Desired therapeutic effects can be expected through administration by dividing the dose into one to 3 times per day.

The construction and effects of the present invention are now illustrated in greater detail with references to specific example of the compounds according to the present invention and their experiments. However, the present invention is not deemed to be limited thereto, so long as they are within the spirit of the present invention.

EXAMPLE 1

2-Methylimidazo[2,1-b]benzothiazole-3-methanol:

In 100 ml of n-butanol were heated 30.0 g of 2-aminobenzothiazole and 25.0 g of propargyl bromide at 100° C. for 6 hours. After cooling, the precipitated crystals were taken out by filtration and recrystallized from water to give 40.0 g of the intermediate. Next, the intermediate was added to 250 ml of sodium ethoxideethanol solution (Na, 3.3 g). The mixture was heated under reflux for one hour. After completion of the reaction, the solvent was removed and water was added to the residue. The precipitated crystals were taken out by filtration to give 22.4 g of 2-methylimidazo[2,1-b]benzothiazole. The benzothiazole was added to a mixture of 300 ml of dry dimethylformamide and 30.0 ml of phosphorus oxychloride followed by heating at 60° C. for 6 hours. After completion of the reaction, the reaction mixture was poured onto 1 liter of chilled water and then was neutralized with ammonium hydroxide. Then, the precipitated crystals were taken out by filtration. The thus obtained formyl compound, 20.5 g, was suspended in 300 ml of methanol and 1.5 g of sodium borohydride was added to the suspension followed by stirring at room temperature for 2 hours. After methanol was removed, the residue was treated with 200 ml of water and filtered to give 20.0 g of the title compound.

Melting Point: 206.0° C. (decomposed), NMR δ (DMSO-d$_6$), 2.27 (s, 3H, CH$_3$), 4.78 (d, 2H, CH$_2$), 5.28 (t, 1H, OH).

EXAMPLE 2

2-Methylimidazo[2,1-b]benzothiazole-3-methanol hydrochloride:

2-Methylimida[2,1-b]benzothiazole-3-methanol, 2.18 g, was dissolved in ethanol and an excess amount of conc. hydrochloric acid was added to the solution. The mixture was then evaporated to dryness. Recrystallization from ethanol gave 1.53 g of the title compound.

Melting Point: 200.0° C. (decomposed), NMR δ (DMSO-d$_6$), 2.43 (s, 3H, CH$_2$), 4.86 (s, 2H, CH$_2$).

EXAMPLE 3

Imidazo[2,1-b]benzothiazole-3-methanol:

In 250 ml of n-butanol were heated 10.0 g of 2-aminobenzothiazole and 30 ml of 40% chloroacetaldehyde at 90° C. for 27 hours. After the solvent was removed (evaporated to dryness), the residue was crystallized in isopropanol-acetone to give 6.2 g of imidazo[2,1-b]benzothiazole. Subsequently, 4.0 g of the crystals were added to a mixture of 50 ml of dry dimethylformamide and 3.5 ml of phosphorus oxychloride followed by heating at 60° C. for 3 hours and at 75° C. for 6 hours. After completion of the reaction, the reaction mixture was poured onto ice water. After neutralizing with potassium carbonate, the mixture was extracted with ethyl acetate. The ethyl acetate was removed to give 2.2 g of 3-formylimidazo[2,1-b]benzothiazole. The thus obtained formyl compound, 1.3 g, was added to 20 ml of ethanol and furthermore 0.1 g of sodium borohydride was added to the mixture while stirring under ice cooling. After stirring at the same temperature for 10 minutes, the solvent was removed. The residue was treated with water and filtered to give 1.2 g of the title compound.

Melting Point: 183.0°–184.5° C., NMR δ (DMSO-d$_6$), 4.81 (s, 2H, CH$_2$), 5.44 (s, 1H, OH), 7.16 (s, 1H, skeleton).

EXAMPLE 4

3-(1-Hydroxyethyl)-2-methylimidazo[2,1-b]benzothiazole:

3-Formyl-2-methylimidazo[2,1-b]benzothiazole, 4.3 g, was suspended in 40 ml of dry tetrahydrofuran. Under ice cooling, a tetrahydrofuran solution (0.02 mol) of methyl magnesium bromide was added to the suspension in a nitrogen flow followed by stirring at room temperature for 30 minutes. After completion of the reaction, the reaction mixture was acidified with diluted acetic acid. The solvent was removed under reduced pressure followed by extraction with ethyl acetate. The residue obtained from the ethyl acetate phase was crystallized with ether to give 4.1 g of the title compound.

Melting Point: 173.0°–174.0° C., NMR δ (DMSO-d$_6$), 1.52 (d, 3H, CH3), 2.27 (s, 3H, CH3), 5.25 (m, 1H, CH).

EXAMPLE 5

3(α-Hydroxy)butyl-2-methylimidazo[2,1-b]benzothiazole:

3-Formyl-2-methylimidazo[2,1-b]benzothiazole, 2.16 g, was dissolved in 30 ml of dry tetrahydrofuran. Under ice cooling, 0.01 mol of a solution of propyl magnesium bromide in tetrahydrofuran was dropwise added to the solution. After stirring at room temperature for one hour, ice water was poured onto the reaction mixture followed by extraction with chloroform. The chloroform was removed to give 1.80 g of the title compound.

Melting Point: 250.0°–252.0° C., NMR δ (CDCl$_3$), 0.90 (t, 3H, CH$_2$CH$_2$CH$_3$), 2.22 (s, 3H, CH$_3$), 5.07 (t, 1H, CH).

EXAMPLE 6

3(α-Hydroxy-1-methyl)ethyl-2-methylimidazo[2,1-b]benzothiazole:

2-Methylimidazo[2,1-b]benzothiazole, 18.8 g, was suspended in 100 ml of dry tetrahydrofuran. Under cooling (at −78° C.), 100 ml of a solution of n-butyl lithium in n-hexane was dropwise added to the suspension over 15 minutes. After completion of the dropwise addition, the temperature was gradually raised and stirring was performed at 0° C. for 30 minutes. The mixture was again cooled to −78° C. After adding an excess of dry ice, the temperature was gradually raised and stirring was performed at 0° C. for 30 minutes. Under ice cooling, 200 ml of 2N sodium hydroxide solution was added to the reaction solution. After washing with ether, the aqueous phase was neutralized with acetic acid and the precipitated crystals were taken out by filtration. The crystals were stirred in 300 ml of chloroform for 30 minutes and 6.0 g of 2-methylimidazo[2,1-b]benzothiazole-3-carboxylic acid was obtained as the insoluble matter in chloroform.

Subsequently, 6.0 g of 2-methylimidazo[2,1-b]benzothiazole-3-carboxylic acid was suspended in 100 ml of dry dimethylformamide. Under ice cooling, 1.5 g of 60% sodium hydride was added to the suspension. After stirring for 30 minutes, 6.0 g of ethyl iodide was added to the mixture followed by heating at 40° C. overnight. After completion of the reaction, the solvent was removed under reduced pressure. Ether and water were added to the residue, which was fractionated. The residue obtained from the ether phase was crystallized with n-hexane to give 4.0 g of ethyl 2-methylimidazo[2,1-b]benzothiazole-3-carboxylate.

Furthermore, 1.5 g of ethyl 2-methylimidazo[2,1-b]benzothiazole-3-carboxylate was dissolved in 30 ml of dry tetrahydrofuran. Under ice cooling, 10 ml of methyl magnesium bromide was added to the solution. The mixture was stirred at room temperature for 30 minutes and then was refluxed for 2 hours. After the solvent was removed, ethyl acetate and water were added to the residue followed by separation. The ethyl acetate was evaporated, and the residue was recrystallized from ethanol to give 1.0 g of the title compound.

Melting Point: 186.0°–187.0° C., NMR δ (CDCl$_3$), 1.78 (s, 6H, (CH$_3$)$_2$), 2.42 (s, 3H, CH$_3$).

EXAMPLE 7

3(αHydroxy)benzyl-2-methylimidazo[2,1-b]benzothiazole:

3-Formyl-2-methylimidazo[2,1-b]benzothiazole, 2.16 g, was dissolved in 30 ml of dry tetrahydrofuran. Under ice cooling, 0.01 mol of a solution of phenyl magnesium bromide in tetrahydrofuran was dropwise added to the solution. After stirring at room temperature for one hour, ice water was poured onto the reaction mixture followed by extraction with chloroform. From the chloroform phase, 1.91 g of the title compound was obtained.

Melting Point: 122.5°–123.5° C., NMR δ (DMSO-d$_6$), 2.27 (s, 3H, CH$_3$), 6.23 (s, 1H, CH).

EXAMPLE 8

2-Ethylimidazo[2,1-b]benzothiazole-3-methanol:

After 5.40 g of 2-aminobenzothiazole and 7.52 g of 1-bromo-2-butanone were allowed to stand in 40 ml of methyl ethyl ketone at room temperature overnight, 40 ml of water was added to the reaction mixture. Methyl ethyl ketone was distilled off on a water bath of 50° C. under reduced pressure. The residue was crystallized with ether and the crystals were then taken out by filtration to give 8.0 g of 2-ethylimidazo[2,1-b]benzothiazole.

Subsequently, 4.3 g of 2-ethylimidazo[2,1-b]-benzothiazole was added to a solution prepared from 11 g of phosphorus oxychloride and 20 ml of dimethylformamide followed by heating at 50° C. for 2.5 hours. The reaction mixture was poured onto ice water. After neutralizing with ammonium hydroxide, the precipitated crystals were filtered to give 3.88 g of 3-formyl-2-ethylimidazo[2,1-b]benzothiazole.

Furthermore, 3.88 g of 3-formyl-2-ethylimidazo[2,1-b]benzothiazole was suspended in 30 ml of methanol and 1.0 g of sodium borohydride was added to the suspension followed by refluxing for one hour. After completion of the reaction, the reaction solution was evaporated to dryness and the residue was washed with water. The crystals obtained were recrystallized from ethanol to give 2.48 g of the title compound.

Melting Point: 180.0°–182.0° C., NMR δ (DMSO-d$_6$), 1.20(t, 3H, CH$_2$CH$_3$), 2.60 (q, 2H, CH$_2$CH$_3$), 4.76 (d, 2H, CH$_2$), 5.26 (t, 1H, OH).

EXAMPLE 9

7-Methoxy-2-methylimidazo[2,1-b]benzothiazole-3-methanol:

In 100 ml of n-butanol was dissolved 5.0 g of 2-amino-6-methoxybenzothiazole. With heating at 100° C., 25.0 g of propargyl bromide was dropwise added to the solution over 2 hours. The mixture was heated for a further 2 hours. After completion of the reaction, the solvent was evaporated to dryness. After the residue was crystallized with acetone, the crystals were recrystallized from isopropyl alcohol to give 25.1 g of 2-imino-6-methoxy-3-propargylbenzothiazole hydrobromide. The hydrobromide, 24.0 g, was added to sodium ethoxideethanol solution(Na, 2.0 g) followed by refluxing for 1.5 hours. After the reaction mixture was evaporated to dryness, water and ethyl acetate were added to the residue followed by separation. The residue obtained from the ethyl acetate phase was dissolved in ethanol and reacted with hydrochloric acid to convert the same into the hydrochloride. Recrystallization from 95% ethanol gave 17.3 g of 7-methoxy-2-methylimidazo[2,1-b]benzothiazole hydrochloride. The hydrochloride, 17.0 g, was added to a mixture of 10 ml of phosphorus oxychloride and 180 ml of dry dimethylformamide. After stirring at room temperature for one hour, the mixture was heated at 60° C. for 7 hours. The reaction solution was evaporated to dryness and the residue was dissolved in water. The solution was alkalized with potassium carbonate and extracted with chloroform. From the chloroform phase, 14.2 g of 3-formyl-7-methoxy-2-methylimidazo[2,1-b]benzothiazole was obtained. The obtained formyl compound, 3.7 g, was suspended in methanol and treated with 1.0 g of sodium borohydride. The reaction mixture was evaporated to dryness, and the obtained residue was recrystallized from ethanol to give 3.5 g of the title compound.

Melting Point: 203.5°–204.0° C., NMR δ (DMSO-d$_6$), 2.25 (s, 3H, CH$_3$), 3.80 (s, 3H, OCH$_3$), 4.74 (d, 2H, CH$_2$), 5.25 (t, 1H, OH), 7.05 (q, 1H, skeleton), 7.55 (d, 1 H, skeleton), 7.83 (d, 1H, skeleton).

EXAMPLE 10

6,7,8-Trimethoxy-2-methylimidazo[2,1-b]benzothiazole-3-methanol:

In 200 ml of acetic acid were dissolved 22.0 g of 3,4,5-trimethoxyaniline and 30.0 g of ammonium thiocyanate. Under ice cooling, 20.0 ml of a solution of 20.0 g of bromine in acetic acid was dropwise added to the solution over one hour. After allowing to stand at room temperature overnight, 200 ml of water was added to the mixture. The mixture was concentrated at 60° C. to about half and rendered alkaline with ammonia water. The precipitated crystals, 30.1 g, were taken out by filtration. The crystals were refluxed in an aqueous ethanol solution of sodium sulfite for one hour to give 13.6 g of 2-amino-5,6,7-trimethoxybenzothiazole. The compound, 9.6 g, was reacted with 9.6 g of propargyl bromide to give 7.6 g of 2-imino-5,6,7-trimethoxy 3-propargylbenzothiazole hydrobromide. The hydrobromide, 5.4 g, was cyclized with sodium ethoxide (Na, 0.4 g), which was then reacted with hydrochloric acid to form the hydrochloride. The hydrochloride, 5.4 g, was added to a mixture of 6 ml of phosphorus oxychloride and 25 ml of dry dimethylformamide. After stirring at room temperature for one hour, the mixture was heated at 60° C for 7 hours. The reaction solution was evaporated to dryness and the residue was dissolved in water. The solution was alkalized with potassium carbonate and extracted with chloroform. From the chloroform phase, 3.21 g of 3-formyl-7-methoxy-2-methylimidazo[2,1-b]benzothiazole was obtained. The obtained formyl compound was dissolved in 50 ml of ethanol and 3.1 g of sodium borohydride was added to the solution. After stirring at room temperature for one hour, the reaction mixture was warmed at 50° C. for 15 minutes. The reaction mixture was evaporated to dryness and the residue was treated with water. The mixture was filtered and were recrystallized from isopropyl alcohol to give 2.5 g of the title compound.

Melting Point: 195.5°–196.5° C., NMR δ (DMSO-d$_6$), 2.23 (s, 3H, CH$_3$), 3.80 (s, 3H, OCH$_3$), 3.88 (s, 3H, OCH$_3$), 4.00 (s, 3H, OCH$_3$), 4.76 (d, 2H, CH$_2$), 5.33 (t, 1 H, OH), 7.39 (s, 1 H, skeleton).

EXAMPLE 11

7-Fluoro-2-methylimidazo[2,1-b]benzothiazole-3-methanol:

In 800 ml of n-butanol was dissolved 25.0 g of 2-amino-6-fluorobenzothiazole. With heating at 100° C., 25.0 g of propargyl bromide was dropwise added to the solution. After completion of the dropwise addition, the mixture was heated for 4 hours. The precipitated crystals were taken out by filtration and recrystallized from water to give 26.5 g of 2-imino-6-fluoro-3-propargylbenzothiazole hydrobromide. The hydrobromide, 26.5 g, was added to a mixture of 2.54 g of sodium and 70 ml of ethanol at room temperature followed by refluxing for one hour. After completion of the reaction, the solvent was removed and, water and ethyl acetate were added to the residue followed by separation. After 2N hydrochloric acid was added to the residue obtained from the ethyl acetate phase, water was evaporated to give 20.7 g of 7-fluoro-2-methylimidazo[2,1-b]benzothiazole hydrochloride.

The hydrochloride, 20.7 g, was added to 59.5 g of phosphorus oxychloride and 200 ml of dimethylformamide followed by heating at 60° C. for 3 hours. After completion of the reaction, the reaction solution was poured onto ice water containing sodium carbonate. The precipitated crystals were taken out by filtration and recrystallized from ethanol to give 8.77 g of 7-fluoro-3-formyl-3-methylimidazo[2,1-b]benzothiazole. Subsequently, the resulting formyl compound and 1.00 g of sodium borohydride were refluxed in ethanol for one hour. After completion of the reaction, ethanol was removed and the residue was recrystallized from methanol to give 2.74 g of the title compound.

Melting Point: 230.0°–235.0° C., NMR δ (DMSO-d$_6$), 2.80 (s, 3H, CH$_3$), 4.80 (d, 2H, CH$_2$), 5.32 (t, 1H, OH).

EXAMPLE 12

2-Methylimidazo[2,1-b]benzothiazole-3-methanol methyl ether:

In 30 ml of dry dimethylformamide was suspended 2.18 g of 2-methylimidazo[2,1-b]benzothiazole-3-methanol and, 0.50 g of 60% sodium hydride was added to the suspension followed by stirring at room temperature for minutes. After 1.74 g of methyl iodide was added thereto, the mixture was stirred for one hour. Then ice water was added to the reaction mixture followed by extracting with ethyl acetate. After the ethyl acetate was removed, 1.41 g of the title compound was obtained.

Melting Point: 137.0°–138.0° C., NMR δ (CDCl$_3$), 2.39 (s, 3H, CH$_3$), 3.36 (s, 3H, OCH$_2$), 4.73 (s, 2H, CH$_2$).

EXAMPLES 13 and 14

Compounds shown in the Table 1 below were synthesized in a manner similar to Example 12.

TABLE 1

| Example | Product | Melting Point (20 C.) | NMR | Yield (%) |
|---|---|---|---|---|
| 13 | 2-Methylimidazo-[2,1-b]benzothiazole-3-methanol isopropyl ether hydrochloride | — | δ (DMSO-d$_6$) 1.19 (d, 6H, CH(CH$_3$)$_2$), 2.43 (s, 3H, CH$_3$), 3.78 (m, 1H, CH(CH$_3$)$_2$), 4.88 (s, 2H, CH$_2$) | 80.7 |
| 14 | 2-Methylimidazo-[2,1-b]benzothiazole-3-methanol (4-methoxy-benzyl) ether | 115.0 | δ (CDCl$_3$) 2.32 (s, 3H, CH$_3$), 2.80 (s, 2H, CH$_2$), 3.79 (s, 3H, OCH$_3$), 4,49 (s, 2H, CH$_2$) | 74.6 |

EXAMPLE 15

3-Butanoyloxymethyl-2-methylimidazo[2,1-b]benzothiazole

In 30 ml of pyridine were heated 3.00 g of 2-methylimidazo[2,1-b]benzothiazole-3-methanol and 5.00 g of butyric anhydride at 100° C. for one hour. The reaction mixture was then evaporated to dryness and the residue was dissolved in ethyl acetate. The solution was washed with water. After drying over Glauber's salt, the ethyl acetate phase was evaporated to dryness under reduced pressure. The residue was dissolved in acetone and a solution of 1.24 g of oxalic acid in acetone was added to the solution. The precipitated crystals were taken out by filtration to give 3.15 g of the title compound.

Melting Point: 122.0° C. (decomposed), NMR δ (DMSO-d$_6$), 1.82 (t, 3H, CH$_2$CH$_3$), 1.3–1.7 (m, 2H, CH$_3$), 2.28 (t, 2H, CH$_2$CH$_3$), 2.32 (s, 3H, CH$_3$), 5.47 (s, 2H, CH$_2$).

EXAMPLE 16

3-Nonanoyloxymethyl-2-methylimidazo[2,1-b]benzothiazole oxalate:

In 50 ml of dry dimethylformamide was suspended 3.27 g of 2-methylimidazo[2,1-b]benzothiazole-3-methanol. Then, 0.72 g of 60% sodium hydride was added to the suspension. After stirring for 30 minutes, 3.18 g of nonanoyl chloride was added to the mixture followed by stirring at room temperature for 3 hours.

The reaction solution was poured onto ice water and extracted with chloroform. After drying over Glauber's salt, the chloroform phase was evaporated to dryness under reduced pressure. The residue was dissolved in acetone and a solution of 1.35 g of oxalic acid in acetone was added to the solution. The precipitated crystals were taken out by filtration to give 4.03 g of the title compound.

Melting Point: 125.0° C. (decomposed), NMR $\delta$ (DMSO-$d_6$), 1.83 (t, 3H, $CH_3$), 2.33 (s, 3H, $CH_3$), 5.48 (s, 2H, $CH_3$).

EXAMPLE 17

3-(3′,5′,5′-Trimethyl)hexanoyloxymethyl-2-methylimidazo-[2,1-b]benzothiazole oxalate:

In 50 ml of dry dimethylformamide was suspended 3.27 g of 2 methylimidazo[2,1-b]benzothiazole-3-methanol. Then, 0.72 g of 60% sodium hydride was added to the suspension. After stirring for 30 minutes, 3.18 g of 3,5,5-trimethylhexanoyl chloride was added to the mixture followed by stirring at room temperature for 3 hours. The reaction solution was poured onto ice water and extracted with chloroform. After drying over Glauber's salt, the chloroform phase was evaporated to dryness under reduced pressure. The residue was dissolved in acetone and a solution of 1.35 g of oxalic acid in acetone was added to the solution. The precipitated crystals were taken out by filtration to give 3.77 g of the title compound.

Melting Point: 116.0°–117.0° C., NMR $\delta$ (DMSO-$d_6$), 0.74 (s, 9H, $(CH_3)_3$), 0.83 (d, 3H, $CH_3$), 2.33 (s, 3H, $CH_3$), 5.50 (s, 2H, $CH_2$).

EXAMPLE 18

3-o-Methoxybenzoyloxy-2-methylimidazo[2,1-b]benzothiazole:

In 50 ml of dry dimethylformamide was suspended 3.00 g of 2-methylimidazo[2,1-b]benzothiazole-3-methanol. Then, 1.12 g of 60% sodium hydride was added to the suspension. After stirring for 30 minutes, 3.00 g of o-methoxybenzoyl chloride was added to the mixture followed by stirring at room temperature for 3 hours. Ice water was added to the reaction solution and the system extracted with chloroform. After the chloroform was removed, 2.60 g of the title compound was obtained.

Melting Point: 156.5°–157.5° C., NMR $\delta$ (CDCl$_3$), 2.48 (s, 3H, $CH_3$), 3.73 (s, 3H, $OCH_3$), 5.66 (s, 2H, $CH_2$).

EXAMPLE 19

2-Methyl-3-thenoyloxymethylimidazo[2,1-b]benzothiazole:

In 30 ml of dry dimethylformamide was suspended 2.18 g of 2-methylimidazo[2,1-b]benzothiazole-3-methanol. Then, 0.50 g of 60% sodium hydride was added to the suspension. After stirring for 30 minutes, 1.76 g of thenoyl chloride was added to the mixture followed by stirring at room temperature for 3 hours. Ice water was added to the reaction mixture and the system extracted with chloroform. After the chloroform was removed, 1.76 g of the title compound was obtained.

Melting Point: 152.0°–152.2° C., NMR $\delta$ (CDCl$_3$), 3.50 (s, 3H, $CH_3$), 5.60 (s, 2H, $CH_2$).

EXAMPLE 20

2-Methylimidazo[2,1-b]benzothiazole 3-methyl ethyl carbamate:

In 30 ml of dry dimethylformamide was suspended 2.18 g of 2 methylimidazo[2,1-b]benzothiazole-3-methanol. Then, 0.90 g of ethyl isocyanate was added to the suspension. After stirring at 50° C. for 10 minutes and then at room temperature for one hour, the solvent was removed. The residue was recrystallized from ethanol to give 2.00 g of the title compound.

Melting Point: 156.0° C. (decomposed), NMR $\delta$ (DMSO-$d_6$), 1.00 (t, 3H, $CH_2CH_3$), 2.33 (s, 3H, $CH_3$), 3.01 (q, 2H, $CH_2CH_3$), 5.41 (s, 2H, $CH_2$).

EXAMPLE 21

| (Preparation of tablets) | |
| --- | --- |
| Compound (Example 1) of this invention | 250 g |
| Lactose | 620 g |
| Corn starch | 400 g |
| Hydroxypropyl cellulose | 20 g |
| Magnesium stearate | 10 g |

After the compound of the present invention, lactose and corn starch described above were uniformly mixed, 5 w/v% ethanolic solution of hydroxypropyl cellulose was added to the mixture. The mixture was kneaded to prepare into granules. After graining through a sieve of 16 mesh, tableting was performed in a conventional manner to prepare tablets having a weight of 130 mg and a diameter of 7 mm and containing 25 mg of the compound, per 1 tablet.

EXAMPLE 22

| (Preparation of capsules) | |
| --- | --- |
| Compound (Example 9) of this invention | 250 g |
| Lactose | 620 g |
| Avicel | 620 g |
| Magnesium stearate | 10 g |

After the compound of the present invention, lactose, Avicel and stearic magnesium were thoroughly mixed to become homogeneous, the mixture was filled up in No. 3 capsules to prepare capsules having a weight of the content being 150 mg and containing 25 mg of the compound, per 1 capsule.

EXAMPLE 23

| (Preparation of granules) | |
| --- | --- |
| Compound (Example 4) of this invention | 100 g |
| White sugar powders | 300 g |
| Lactose | 200 g |
| Corn starch | 390 g |
| Hydroxypropyl cellulose | 10 g |

After the compound of the present invention, white sugar powders, lactose and corn starch described above were thoroughly mixed to become homogeneous, a 20% hydrated ethanolic solution of 5% hydroxypropyl cellulose was added to the mixture. The mixture was kneaded and then grained through a sieve of 24 mesh. After drying, the grains were passed through a sieve of mesh for graining. Per 1 g of the granules, 100 mg of the compound was contained.

EXAMPLE 24

| (Preparation of granulates) | |
|---|---|
| Compound (Example 1) of this invention | 50 g |
| Lactose | 400 g |
| Corn starch | 300 g |
| Avicel | 620 g |
| Polyvinylpyrrolidone | 10 g |

After the compound of the present invention, lactose, corn starch and Avicel described above were uniformly mixed, a 10 w/v% methanolic solution of polyvinylpyrrolidone was added to the mixture. After kneading the mixture, the mixture was ground and grained with a grinder. After drying, the mixture was passed through a sieve of 20 mesh for granulation. Per 1 g of the granulates, 50 mg of the compound was contained.

EXAMPLE 25

| (Preparation of injections) | |
|---|---|
| Compound (Example 1) of this invention | 2.5 g |
| Polyethylene glycol | 50 ml |
| Ethanol | 50 ml |
| Distilled water for injection | 900 ml |

The compound of the present invention described above was dissolved in ethanol and the solution was made 1,000 ml with distilled water for injection. The mixture was aseptically filtered through a suitable filter paper. The resulting solution was divided into ampoules to prepare injections.

EXPERIMENT 1

Antiulcer activity against aspirin-induced ulcer model

Test Method:

A suspension of each test compound in a 5% gum arabic aqueous solution was orally given to Wistar strain male rats (at the age of 7 to 8 weeks, weighing 180 to 250 g; 6–8 rats in the group administered with the test compound; 14–16 rats in the control group) fasted for 24 hours at a dose of 100 mg of the test compound/5 ml/kg. Thirty minutes after administration, aspirin was further orally administered at a dose of 200 mg/kg. Seven hours after administration of aspirin, the stomach was excised under ethereal anesthesia and spotted and linear erosion and a long diameter of any ulcer were microscopically measured to determine an ulcer index and an inhibition rate.

In the control group, a 5% gum arabic aqueous solution was orally administered at a dose of 5 ml/kg.

Results:

The results are shown in the Table 2 below.

TABLE 2

| Example No. | No. of Rats | Aspirin Induced Ulcer | |
|---|---|---|---|
| | | Ulcer Index $(mm^2)$ | Inhibition Rate (%) |
| Control | 14 | 57.4 ± 5.3 | — |
| Example 1 | 7 | 23.3 ± 5.1*** | 59.4 |
| Example 5 | 6 | 43.8 ± 10.3 | 23.7 |
| Example 7 | 7 | 39.6 ± 3.7* | 31.0 |
| Control | 14 | 66.8 ± 6.5 | — |
| Example 2 | 7 | 36.0 ± 5.8** | 46.1 |
| Example 18 | 7 | 45.3 ± 10.4 | 32.2 |
| Example 19 | 7 | 63.7 ± 8.1 | 4.6 |
| Control | 16 | 70.9 ± 6.3 | — |
| Example 4 | 8 | 8.0 ± 2.9** | 88.7 |

TABLE 2-continued

| Example No. | No. of Rats | Aspirin Induced Ulcer | |
|---|---|---|---|
| | | Ulcer Index $(mm^2)$ | Inhibition Rate (%) |
| Example 6 | 8 | 55.1 ± 8.7 | 22.3 |
| Example 11 | 8 | 34.2 ± 2.2** | 51.8 |
| Control | 14 | 76.2 ± 6.6 | — |
| Example 9 | 7 | 64.8 ± 7.5 | 15.0 |
| Example 10 | 7 | 53.7 ± 8.3 | 29.5 |
| Example 12 | 7 | 49.9 ± 5.4* | 34.5 |
| Example 20 | 7 | 56.2 ± 6.8 | 26.2 |
| Control | 15 | 84.1 ± 4.6 | — |
| Example 13 | 8 | 24.4 ± 3.3** | 71.0 |
| Example 14 | 8 | 71.5 ± 8.0 | 15.0 |

*$P < 0.05$
**$P < 0.01$
***$P < 0.001$

EXPERIMENT 2

Antiulcer activity against water-immersion stress ulcer

Test Method:

A suspension of each test compound in a 5% gum arabic aqueous solution was orally given to Wistar strain male rats (at the age of 7 to 8 weeks, weighing 180 to 250 g; 7–9 rats in the group administered with the test compound; 10–16 rats in the control group) fasted for 24 hours at a dose of 100 mg of the test compound/5 ml/kg. Thirty minutes after administration, the animal was immersed in a water bath at 22°±1° C. up to the xiphisternum using a stress cage made by Tokyo University, Faculty of Pharmacology, to apply a stress load for 6 hours. After applying the stress load, the rats had the cervical vertebra dislocated to death. Then, the stomach was excised and, spotted and linear erosion and a long diameter of any ulcer were microscopically measured to determine an ulcer index and an inhibition rate.

In the control group, a 5% gum arabic aqueous solution was orally administered at a dose of 5 ml/kg.

Results:

The results are shown in the Table 3 below.

TABLE 3

| Example No. | No. of Rats | Water-Immersion Stress Ulcer | |
|---|---|---|---|
| | | Ulcer Index $(mm^2)$ | Inhibition Rate (%) |
| Control | 14 | 21.5 ± 2.7 | — |
| Example 1 | 7 | 4.3 ± 0.9*** | 80.0 |
| Example 5 | 7 | 20.4 ± 4.2 | 5.1 |
| Example 7 | 7 | 17.9 ± 4.5 | 16.7 |
| Control | 14 | 23.3 ± 3.1 | — |
| Example 2 | 7 | 4.6 ± 1.1*** | 80.3 |
| Example 18 | 7 | 13.5 ± 4.1 | 42.1 |
| Example 19 | 7 | 11.3 ± 2.6* | 51.5 |
| Control | 16 | 23.7 ± 3.8 | — |
| Example 4 | 8 | 7.3 ± 2.5** | 69.2 |
| Example 6 | 8 | 11.7 ± 4.5 | 50.6 |
| Example 11 | 8 | 10.9 ± 4.4 | 54.0 |
| Control | 10 | 16.3 ± 4.6 | — |
| Example 8 | 9 | 8.1 ± 2.2 | 50.3 |
| Control | 14 | 13.2 ± 2.5 | — |
| Example 9 | 7 | 6.4 ± 1.2* | 51.5 |
| Example 10 | 7 | 9.6 ± 2.1 | 27.3 |
| Example 12 | 7 | 2.2 ± 0.4*** | 83.3 |
| Example 20 | 7 | 4.0 ± 1.3** | 69.7 |
| Control | 15 | 12.3 ± 2.1 | — |
| Example 14 | 8 | 7.5 ± 2.2 | 39.0 |

*$P < 0.05$
**$P < 0.01$
***$P < 0.001$

EXPERIMENT 3

Antiulcer activity against ethanol-induced ulcer model

Test Method:

A suspension of each test compound in a 5% gum arabic aqueous solution was orally given to Wistar strain male rats (at the age of 7 to 8 weeks, weighing 180 to 250 g; 5 rats in the group administered with the test compound; 9 rats in the control group) fasted for hours at a dose of 100 mg of any the test compound/5 ml/kg. Thirty minutes after administration, absolute ethanol was further orally administered at a dose of 5 ml/kg. One hour after administration of absolute ethanol, the stomach was excised under ethereal anesthesia and spotted and linear erosion and a long diameter of ulcer were microscopically measured to determine an ulcer index and an inhibition rate.

In the control group, a 5% gum arabic aqueous solution was orally administered at a dose of 5 ml/kg. Results:

The results are shown in the Table 4 below.

to 250 g; 7–9 rats in the group administered with the test compound; 14–17 rats in the control group) fasted for 24 hours at a dose of 100 mg of the test compound/5 ml/kg. Thirty minutes after administration, pyloric ligature was made under ethereal anesthesia. Four hours thereafter, the stomach was excised under ethereal anesthesia to collect gastric juice. The collected gastric juice was centrifuged (2500 rpm) at 4° C. for 10 minutes. After the supernatant was collected, the amount of the gastric juice and its pH were measured using a pH meter. Furthermore, the amount of free hydrochloric acid and the total acidity were measured with Töpfer reagent and phenolphthalein reagent, respectively. Using a part of the gastric juice, pepsin output in the gastric juice was measured using casein as a substrate in a manner similar to the method of Anson et al.

In the control group, a 5% gum arabic aqueous solution was orally administered at a dose of 5 ml/kg. Results:

The results are shown in the Table 5 below.

TABLE 5

| Example No. | No. of Rats | Volume (ml) | Volume Inhibition Rate (%) | pH | Free HCl (mEq/l) | Acidity (mEq/l) | Pepsin Activity (units/ml) | Pepsin Output (units/hr) |
| --- | --- | --- | --- | --- | --- | --- | --- | --- |
| Control | 14 | 5.9 ± 0.5 | — | 1.47 ± 0.03 | 47.6 ± 3.2 | 71.3 ± 3.6 | 104.7 ± 1.7 | 153.8 ± 12.8 |
| Ex. 1 | 7 | 2.8 ± 0.4*** | 52.5 | 2.94 ± 0.30** | 9.4 ± 3.1*** | 49.0 ± 5.9** | 90.3 ± 5.9 | 59.6 ± 6.8*** |
| Ex. 7 | 7 | 5.4 ± 0.6 | 8.5 | 1.65 ± 0.13 | 39.7 ± 5.0 | 69.1 ± 7.0 | 99.5 ± 4.1 | 135.0 ± 18.1 |
| Ex. 5 | 7 | 6.7 ± 0.7 | −13.6 | 2.17 ± 0.12** | 10.4 ± 2.1*** | 45.0 ± 5.6*** | 86.2 ± 1.9*** | 139.6 ± 16.7 |
| Control | 15 | 6.0 ± 0.4 | — | 1.41 ± 0.04 | 55.4 ± 3.7 | 84.9 ± 4.3 | 96.3 ± 1.6 | 144.9 ± 10.6 |
| Ex. 2 | 7 | 2.8 ± 0.4*** | 53.3 | 2.43 ± 0.20** | 15.8 ± 4.5 | 77.3 ± 4.5 | 91.1 ± 8.3 | 58.4 ± 5.2*** |
| Ex. 19 | 7 | 4.9 ± 0.5 | 18.3 | 1.56 ± 0.10 | 48.6 ± 3.4 | 78.9 ± 2.7 | 99.6 ± 2.2 | 122.8 ± 14.4 |
| Ex. 18 | 7 | 8.1 ± 0.8* | −35.0 | 1.45 ± 0.06 | 51.7 ± 5.8 | 82.1 ± 5.0 | 91.4 ± 3.3 | 186.6 ± 24.3 |
| Control | 14 | 6.3 ± 0.6 | — | 1.40 ± 0.03 | 51.1 ± 2.5 | 74.5 ± 2.9 | 99.6 ± 2.6 | 158.4 ± 15.5 |
| Ex. 9 | 7 | 5.3 ± 0.9 | 15.9 | 1.55 ± 0.08 | 42.6 ± 5.2 | 76.2 ± 4.3 | 102.2 ± 3.9 | 135.5 ± 22.7 |
| Ex. 12 | 7 | 2.5 ± 0.1*** | 60.3 | 2.28 ± 0.26* | 23.2 ± 6.9** | 66.7 ± 4.7 | 90.7 ± 4.1 | 55.5 ± 3.9*** |
| Ex. 10 | 7 | 5.2 ± 0.5 | 17.5 | 1.47 ± 0.03 | 50.4 ± 3.2 | 87.3 ± 3.5* | 103.5 ± 1.8 | 133.7 ± 10.8 |
| Ex. 20 | 7 | 5.9 ± 0.3 | 6.3 | 1.89 ± 0.12** | 26.1 ± 5.5*** | 54.5 ± 7.0* | 91.6 ± 1.7* | 136.0 ± 7.2 |

| Example No. | No. of Rats | Volume (ml/100 g) | pH | Free HCl (mcEq/100 g) | Acid Output (mcEq/100 g) | Pepsin Output (mg tyrosine/100 g) |
| --- | --- | --- | --- | --- | --- | --- |
| Control | 17 | 3.21 ± 0.23 | 1.25 ± 0.04 | 229.6 ± 28.4 | 276.1 ± 29.7 | 30.0 ± 2.4 |
| Ex. 13 | 7 | 1.29 ± 0.23** | 2.70 ± 0.53* | 22.3 ± 10.7** | 57.6 ± 16.4** | 13.0 ± 2.3** |
| Ex. 14 | 8 | 2.63 ± 0.35 | 1.42 ± 0.08* | 144.9 ± 35.0 | 196.8 ± 38.0 | 22.4 ± 3.8 |
| Control | 15 | 4.04 ± 0.24 | 1.09 ± 0.03 | 345.0 ± 32.8 | 387.1 ± 33.4 | 39.9 ± 2.7 |
| Ex. 11 | 9 | 1.40 ± 0.34** | 1.58 ± 0.15** | 89.1 ± 35.5** | 118.8 ± 37.2** | 16.7 ± 2.9** |
| Ex. 4 | 9 | 0.69 ± 0.09** | 2.36 ± 0.21** | 8.0 ± 2.9** | 30.8 ± 5.1** | 9.9 ± 1.3** |
| Ex. 6 | 8 | 1.90 ± 0.33** | 1.24 ± 0.07 | 138.6 ± 37.3** | 169.9 ± 38.0** | 23.4 ± 3.9** |

*P < 0.05
**P < 0.01
***P < 0.001

TABLE 4

| Example No. | No. of Rats | Ethanol Induced Ulcer Ulcer Index (mm²) | Ethanol Induced Ulcer Inhibition Rate (%) |
| --- | --- | --- | --- |
| Control | 9 | 86.0 ± 18.2 | — |
| Example 1 | 5 | 4.9 ± 2.6** | 94.3 |
| Example 8 | 5 | 4.1 ± 2.2** | 95.2 |

**P < 0.01

EXPERIMENT 4

Gastric juice secretion inhibition activity

Test Method:

A suspension of each test compound in a 5% gum arabic aqueous solution was orally given to Wistar strain male rats (at the age of 7 to 8 weeks, weighing 180

EXPERIMENT 5

Acute toxicity

Test Method:

A suspension of each test compound in a 5% gum arabic aqueous solution was orally given to ddy strain male mice (at the age of 4 to 5 weeks, weighing 25 to 35 g; 2 to 9 mice in one group). For 7 days after the administration, the mice were observed as to if they were dead or alive. Based on the number of deaths, the $LD_{50}$ value was determined by the Probit method.

Results:

The results are shown in the Table 6 below.

TABLE 6

| Example No. | Dose (mg/kg p.o) | Mortality (No. death/ No. treated) | LD$_{50}$ (mg/kg) |
| --- | --- | --- | --- |
| Example 1 | 4899 | 2/2 | |
| | 4000 | 3/5 | 3587 |
| | 2828 | 1/5 | (2842– |
| | 2000 | 0/4 | 4980) |
| Example 2 | 2449 | 4/5 | |
| | 2236 | 3/5 | 2134 |
| | 2041 | 2/4 | (1900– |
| | 1732 | 0/5 | 2464) |
| Example 4 | 500 | 0/5 | — |
| | 1000 | 0/5 | |
| Example 6 | 500 | 0/5 | — |
| | 1000 | 0/5 | |
| Example 11 | 500 | 0/5 | — |
| | 1000 | 0/5 | |
| Example 12 | 2828 | 6/6 | 1767 |
| | 2000 | 6/9 | (1271– |
| | 1414 | 1/5 | 2090) |
| Example 13 | 500 | 0/5 | — |
| | 1000 | 5/5 | |
| Example 14 | 500 | 0/5 | — |
| | 1000 | 0/5 | |

While the invention has been described in detail and with reference to specific embodiments thereof, it will be apparent to one skilled in the art that various changes and modifications can be made therein without departing from the spirit and scope thereof.

What is claimed is:

1. An imidazo[2,1-b]benzothiazole compound represented by formula (I) and pharmacological acceptable salts thereof:

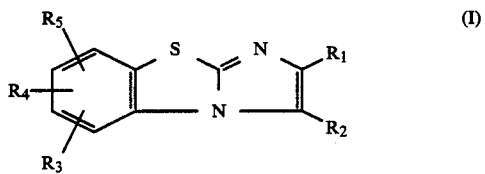

wherein R$_1$ represents a hydrogen atom or a lower alkyl group having 1 to 4 carbon atoms; R$_2$ represents a

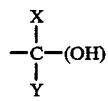

group, wherein X and Y, which may be the same or different, each represents a hydrogen atom, a lower alkyl group having 1 to 4 carbon atoms, a phenyl group, a phenyl group substituted with a lower alkyl group having 1 to 4 carbon atoms, a lower alkoxy group having 1 to 4 carbon atoms or a halogen atom, a —CH$_2$—O—Z group, wherein Z represents a lower alkyl group having 1 to 4 carbon atoms, a benzyl group, a benzyl group substituted with a lower alkyl group having 1 to 4 carbon atoms, a lower alkoxy group having 1 to 4 carbon atoms or a halogen atom of a —CH$_2$—O—CO—W group, wherein W represents an alkyl group having 1 to 8 carbon atoms, an alkylamino group having 1 to 8 carbon atoms, a phenyl group, a phenyl group substituted with a lower alkyl group having 1 to 4 carbon atoms, a lower alkoxy group having 1 to 4 carbon atoms, or a halogen atom or a thienyl group; and R$_3$, R$_4$ and R$_5$, which may be the same or different, each represents a hydrogen atom, a halogen atom or a lower alkoxy group having 1 to 4 carbon atoms.

2. The compound according to claim 1, wherein R$_1$ represents a hydrogen atom or a lower alkyl group having 1 to 4 carbon atoms, and R$_2$ represents a

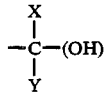

group (wherein X and Y are as defined in formula (I)).

3. The compound according to claim 2, wherein R$_1$ represents a hydrogen atom or a lower alkyl group having 1 to 4 carbon atoms, R$_2$ represents a

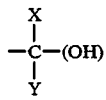

group (wherein X and Y are as defined in formula (I)), and R$_3$, R$_4$ and R$_5$ each represents a hydrogen atom.

4. The compound according to claim 2, wherein R$_1$ represents a hydrogen atom or a lower alkyl group having 1 to 4 carbon atoms, and R$_2$ represents a —CH$_2$OH group.

5. 2-Methylimidazo[2,1-b]benzothiazole-3-methanol.

6. 3-(1-Hydroxyethyl)-2-methylimidazo[2,1-b]benzothiazole.

7. The compound according to claim 1, wherein R$_1$ represents a hydrogen atom or a lower alkyl group having 1 to 4 carbon atoms, and R$_2$ represents a —CH$_2$—O—Z group (wherein Z is as defined in formula (I)).

8. The compound according to claim 7, wherein R$_1$ represents a hydrogen atom or a lower alkyl group having 1 to 4 carbon atoms, R$_2$ represents a —CH$_2$—O—Z group (wherein Z is as defined in formula (I)), and R$_3$, R$_4$ and R$_5$ each represents a hydrogen atom.

9. 2-Methylimidazo[2,1-b]benzothiazole-3-methanol methyl ether.

10. 2-Methylimidazo[2,1-b]benzothiazole-3-methanol isopropyl ether.

11. The compound according to claim 1, wherein R$_1$ represents a hydrogen atom or a lower alkyl group having 1 to 4 carbon atoms, and R$_2$ represents a —CH$_2$—O—CO—W group (wherein W is as defined in formula (I)).

12. The compound according to claim 11, wherein R$_1$ represents a hydrogen atom or a lower alkyl group having 1 to 4 carbon atoms, and R$_2$ represents a CH$_2$—O—CO—W group (wherein W is as defined in formula (I)), and R$_3$, R$_4$ and R$_5$ each represents a hydrogen atom.

13. An antiulcer composition comprising as the effective ingredient a compound represented by formula (I) or pharmacologically acceptable salt thereof according to claim 1, together with a pharmaceutical carrier in combination.

* * * * *